United States Patent [19]

Baldwin et al.

[11] Patent Number: 4,539,318
[45] Date of Patent: Sep. 3, 1985

[54] TERTIARY AMINOHYDROXYPROPOXY SUBSTITUTED THIADIAZOLES, PHARMACEUTICAL COMPOSITIONS AND USE

[75] Inventors: John J. Baldwin, Gwynedd Valley; Gerald S. Ponticello, Lansdale, both of Pa.

[73] Assignee: Merck & Co., Inc., Rahway, N.J.

[21] Appl. No.: 617,296

[22] Filed: Jun. 4, 1984

[51] Int. Cl.³ ............... A61K 31/535; A61K 31/54; C07D 413/14; C07D 417/14
[52] U.S. Cl. ............................ 514/222; 514/229; 514/252; 514/256; 514/269; 514/316; 514/318; 514/326; 544/58.6; 544/58.7; 544/60; 544/115; 544/121; 544/122; 544/123; 544/129; 544/130; 544/238; 544/295; 544/298; 544/333; 544/357; 544/360; 544/367; 546/187; 546/193; 546/209

[58] Field of Search .............. 544/58.6, 58.7, 60, 544/115, 121, 122, 123, 129, 130, 238, 295, 298, 333, 360, 367, 357; 546/187, 193, 209; 424/248.51, 250, 251, 263, 267

[56] References Cited

U.S. PATENT DOCUMENTS

| | | | |
|---|---|---|---|
| 3,655,663 | 4/1972 | Wasson | 544/129 |
| 3,941,789 | 3/1976 | Renth et al. | 424/250 |
| 4,134,983 | 1/1979 | Baldwin | 424/267 |
| 4,440,774 | 4/1984 | Baldwin | 424/267 |

*Primary Examiner*—Robert W. Ramsuer
*Attorney, Agent, or Firm*—Alice O. Robertson; Salvatore C. Mitri

[57] ABSTRACT

Novel tertiary aminohydroxypropoxy substituted thiadiazole compounds exhibit $\alpha_1$-adrenoceptor and serotonin antagonism and are also useful as antihypertensive agents.

5 Claims, No Drawings

TERTIARY AMINOHYDROXYPROPOXY SUBSTITUTED THIADIAZOLES, PHARMACEUTICAL COMPOSITIONS AND USE

SUMMARY OF THE INVENTION

This invention is concerned with a novel compound of structural formula:

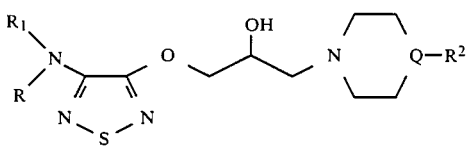

wherein Q is >N- or

or a pharmaceutically acceptable salt thereof and R, $R^1$ and $R^2$ are as defined below, which have $\alpha_1$-adrenoceptor and serotonin blocking properties and hence useful in the treatment of hypertension and certain related conditions.

The invention is also concerned with processes for the preparation of the novel compounds; pharmaceutical formulations comprising one or more of the novel compounds as active ingredient; and a method of treating hypertension, gastrointestinal ulcers, bronchial spasm, varices, hemorrhoids and related congestive disorders, and elevated intraocular pressure.

BACKGROUND OF THE INVENTION

There are various classes of antihypertensive drugs including the diuretics such as hydrochlorothiazide, angiotensin converting enzyme inhibitors such as enalapril, $\beta$-blockers such as timolol, $\alpha$-blockers such as prazosin, and mixed $\beta/\alpha_1$-adrenergic receptor antagonists such as labetolol.

Now, with the present invention there is provided a class of compounds that structurally resemble the well known $\beta$-blockers, with the aryloxypropanolamine skeleton, but which are almost devoid of $\beta$-blocking activity and demonstrate $\alpha_1$-adrenergic receptor antagonism and a component of serotonin antagonism.

DETAILED DESCRIPTION OF THE INVENTION

The novel compounds of this invention have structural formula I:

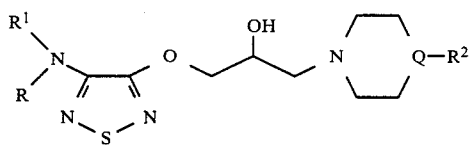

or a pharmaceutically acceptable salt thereof wherein:
R and $R^1$ are independently:
(1) $C_{1-8}$ alkyl, either straight or branched chain,
(2) R and $R^1$ are joined together directly to form, with the nitrogen to which they are attached, pyrolidino or piperidino, or through a heteroatom selected from O, N-($C_{1-3}$ alkyl) and S to form a six-membered heterocycle such as N-($C_{1-3}$ alkyl)-piperazino, or morpholino;

Q is >N- or

and
$R^2$ is
(1) a carbocycle or heterocycle of 6 nuclear atoms, 0, 1 or 2 of which can be nitrogen atoms, and either unsubstituted or substituted with one or more of
(i) $C_{1-3}$ alkyl,
(ii) halo such as chloro, bromo or fluoro,
(iii) hyroxy,
(iv) cyano, or
(v) $C_{1-3}$ alkoxy.

Preferred are those compounds of Formula I, wherein R and $R^1$ are independently $C_{1-3}$ alkyl or taken together form a 6-membered heterocycle containing an additional O, S or N-$C_{1-3}$ alkyl heteroatom; and $R^2$ is phenyl, methoxyphenyl, halophenyl, or halopyridyl, especially 3- or 5-fluoro-2-pyridyl, In the most preferred embodiment, R and $R^1$ are joined to form a morpholino group and Q-$R^2$ is

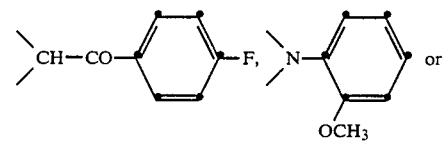

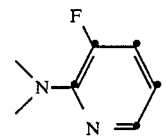

The novel compounds of this invention include all the optical isomer forms as pure enantiomers or as mixtures containing the optical isomers such as racemic mixtures and compounds.

The compounds of the present invention also include the non-toxic pharmaceutically acceptable acid addition and quaternary ammonium salts. The acid addition salts are prepared by treating the compounds with an appropriate amount of a suitable organic or inorganic acid. Examples of useful organic acids are carboxylic acids such as maleic acid, tartaric acid, acetic acid, pamoic acid, oxalic acid, propionic acid, salicyclic acid, succinic acid, citric acid, malic acid, isethionic acid, and the like. Useful inorganic acids are hydrohalo acids such as hydrochloric, hydrobromic, hydriodic, sulfuric, phosphoric acid, or the like.

The novel process of this invention is illustrated as follows:

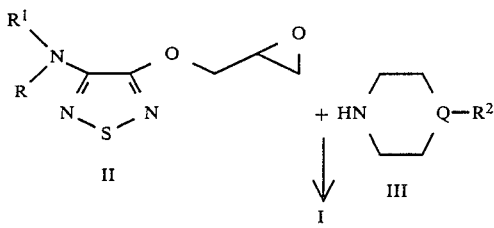

wherein Q is as defined above.

An epoxide II is reacted with an amine of the type III in a suitable solvent such as methanol, ethanol, isopropanol, methylene chloride, THF or the like, at 0° C. to the reflux temperature of the solvent for about 1–48 hours, preferably in isopropanol at about 70° C. for 24 hours, to yield I. The epoxide moiety of II may be, prepared in chiral (R or S) form and if utilized in the above reaction would provide compound I in the (R)- or (S)-conformation, respectively.

The compounds of the present invention are active (1) as $\alpha_1$-adrenergic receptor antagonists, and useful in the treatment of elevated intraocular pressure, and hypertension; and (2) as serotonin antagonists; i.e., they reduce and minimize lesions caused by excessive serotonin release and block serotonin-induced contractions of bronchial tissues and of blooc vessels, arteries and veins. Thus, the compounds of the present invention are useful to treat gastrointestinal ulcers, bronchial spasms, varices, hemorrhoids and similar diseases caused by congestion.

The $\alpha_1$-antagonist activity ($\alpha_1$-blockade) of the present compounds was determined by measuring the ability of representative compounds to block methoxamine induced contraction using cat vas deferens tissue. Several compounds were also shown to bind specifically to the serotonin-$S_2$-receptor using $^3[H]$spiperone as ligand and to the $\alpha_1$-receptor using $^3[H]$prazosin a ligand. Representative examples of the novel compounds demonstrated $\alpha_1$-blockade, $\alpha_1$- and $S_2$-binding in addition to having the aforesaid antihypertensive effect.

The ability of the compounds of the present invention to reduce blood pressure in the SH rat indicates that the compounds and their salts may be useful in treating essential hypertension in humans.

For use as antihypertensives, serotonin, and/or $\alpha_1$-blocking agents, the present compounds can be administered orally or parenterally; i.e., intravenously, interperitoneally, etc. and in any suitable dosage form. The compounds may be offered in a form (a) for oral administration; e.g., as tablets, in combination with other compounding ingredients customarily used such as talc, vegetable oils, polyols, benzyl alcohols, gums, gelatin, starches and other carriers; dissolved or dispersed or emulsified in a suitable liquid carrier; in capsules or encapsulated in a suitable encapsulating material; or (b) for parenteral administration; e.g., dissolved or dispersed in a suitable liquid carrier or emulsified; or (c) transdermal application; or (d) in an ophthalmic formulation for topical ocular administration. The ratio of active compound to compounding ingredients; i.e., carrier, diluent, etc., will vary as the dosage form requires. Whatever dosage form is used, the amount of compound of the present invention administered should be sufficient to effect (a) a reduction in blood pressure of the patient suffering from hypertension and/or (b) desirable level of $\alpha_1$-adrenoceptor blockade in the patient, and/or (c) inhibit serotonin release. Generally, doses of the present compounds of from about 0.01 to about 50 mg/kg and preferably from about 0.1 to about 20 mg/kg of body weight per day may be used. Dosage may be single or multiple depending on the daily total required and the unit dosage.

Following are examples illustrating representative pharmaceutical formulations containing compounds of the present invention. Conventional techniques are used to prepare these formulations.

| TABLET FORMULATION | |
|---|---|
| INGREDIENT | AMOUNT (Mg.) |
| 3-[3-[4-(4-fluorobenzoyl)piperidine-1-yl]-2-hydroxypropoxy]-4-morpholino-1,2,5-thiadiazole | 40.0 |
| calcium phosphate | 120.0 |
| lactose | 50.0 |
| starch | 23.5 |
| magnesium stearate | 1.5 |

| CAPSULE FORMULATION | |
|---|---|
| INGREDIENT | AMOUNT (Mg.) |
| 3-[3-[4-(4-fluorobenzoyl)piperidine-1-yl]-2-hydroxypropoxy]-4-morpholino-1,2,5-thiadiazole | 250 |
| lactose, U.S.P. | 93 |
| talc | 7 |

| INJECTABLE SOLUTION | |
|---|---|
| INGREDIENT | AMOUNT (Mg.) |
| 3-[3-[4-(4-fluorobenzoyl)piperidine-1-yl]-2-hydroxypropoxy]-4-morpholino-1,2,5-thiadiazole | 5 |
| sodium chloride | 9 |
| distilled water, q.s. 1.0 ml. | |

| LIQUID SUSPENSION | |
|---|---|
| INGREDIENT | AMOUNT (Mg.) |
| 3-[3-[4-(4-fluorobenzoyl)piperidine-1-yl]-2-hydroxypropoxy]-4-morpholino-1,2,5-thiadiazole | 5.0 |
| Veegum H.V. | 3.0 |
| methyl paraben | 1.0 |
| kaolin | 10.0 |
| glycerin | 250.0 |
| water, q.s. 1 liter | |

The following examples illustrate preparation of representative compounds of the present invention. Unless otherwise indicated, all parts and percentages are by weight, all temperatures are in degrees Celsius, and all analyses were computed to within 0.4%.

EXAMPLE 1

3-[3-[4-(4-Fluorobenzoyl)piperidine-1-yl]-2-hydroxypropoxy]-4-morpholino-1,2,5-thiadiazole (3)

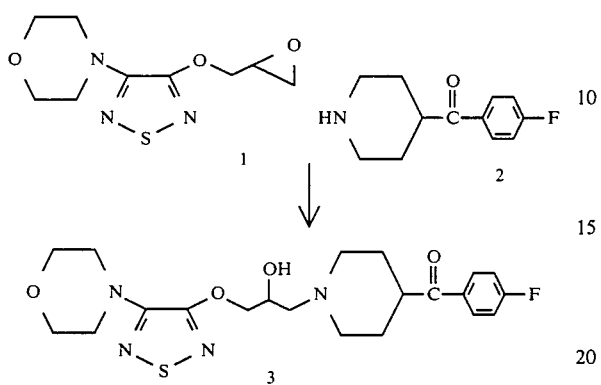

The epoxide 1 (1.23 g, 7 mmol) and the amine 2 (1.45 g, 7 mmol) (prepared from the HCl salt just prior to use) were heated overnight in isopropanol (20) at 40° C. The white product was separated by filtration, washed with isopropanol (about 20 ml), ether and dried invacuo to yield 2.1 g (78%) of 3; m.p. 98°–98.5° C.

Analysis satisfactory for $C_{21}H_{27}FN_4O_4S$.

Employing the procedures substantially as described in Example 1, but using as starting materials, the epoxides and the amines described in Table I, there are produced the tertiary aminohydroxypropoxy substituted thiadiazole compounds also described in Table I in accordance with the following reaction scheme:

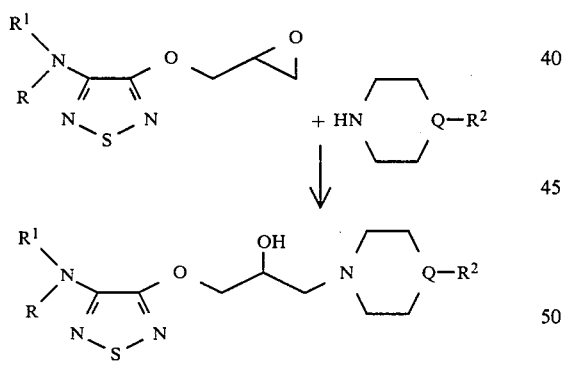

TABLE I and TABLE I-continued list combinations of R, R¹, Q, and R² substituents (structures shown in figure).

What is claimed is:

1. A compound of structural formula:

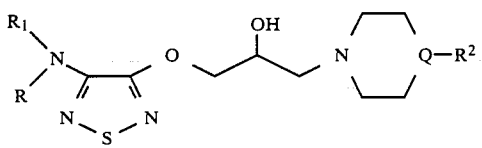

or a pharmaceutically acceptable salt thereof wherein:

R and $R^1$ are independently:

(1) $C_{1-8}$ alkyl, either straight or branched chain, (2) R and $R^1$ are joined together directly to form, with the nitrogen to which they are attached, pyrrolidino or piperidino, or through a heteroatom selected from O, N-($C_{1-3}$ alkyl) and S to form a six-membered heterocycle;

Q is >N- or

and
$R^2$ is (1) a carbocycle or heterocycle of 6 nuclear atoms, 0, 1 or 2 of which can be nitrogen atoms and either unsubstituted or substituted with
   (i) $C_{1-3}$ alkyl,
   (ii) hydroxy,
   (iii) halo,
   (iv) cyano, or
   (v) $C_{1-3}$ alkoxy.

2. The compound of claim 1 or a pharmaceutically acceptable salt thereof wherein R and $R^1$ are independently $C_{1-3}$ alkyl, or taken together with the nitrogen to which they are attached form a 6-membered heterocycle containing an additional heteroatom selected from O, S and N-$C_{1-3}$ alkyl; and $R^2$ is phenyl, methoxyphenyl, halophenyl, or halopyridyl.

3. The compound of claim 2, wherein R and $R^1$ are joined to form a morpholino group and Q-$R^2$ is

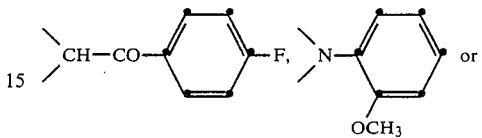

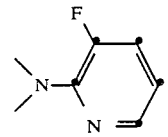

4. A pharmaceutical composition comprising a pharmaceutically acceptable carrier and an effective amount of a compound as defined in claim 1 or a pharmaceutically acceptable salt thereof.

5. A method of antagonizing $\alpha_1$-adrenergic receptors and serotonin release which comprises the administration to a patient in need of such treatment of an effective amount of the compound of claim 1 or a pharmaceutically acceptable salt thereof.

* * * * *